United States Patent
Khoury et al.

(10) Patent No.: US 8,367,092 B2
(45) Date of Patent: Feb. 5, 2013

(54) METHOD FOR MODIFYING THE WETTABILITY AND/OR OTHER BIOCOMPATIBILITY CHARACTERISTICS OF A SURFACE OF A BIOLOGICAL MATERIAL BY THE APPLICATION OF GAS CLUSTER ION BEAM TECHNOLOGY AND BIOLOGICAL MATERIALS MADE THEREBY

(75) Inventors: Joseph Khoury, Dedham, MA (US); Laurence B. Tarrant, Cambridge, MA (US); Sean R. Kirkpatrick, Littleton, MA (US); Richard C. Svrluga, Newton, MA (US)

(73) Assignee: Exogenesis Corporation, Billerica, MA (US)

( * ) Notice: Subject to any disclaimer, the term of this patent is extended or adjusted under 35 U.S.C. 154(b) by 196 days.

(21) Appl. No.: 12/722,126

(22) Filed: Mar. 11, 2010

(65) Prior Publication Data

US 2010/0226897 A1    Sep. 9, 2010

Related U.S. Application Data

(63) Continuation-in-part of application No. 12/210,018, filed on Sep. 12, 2008, now abandoned.

(60) Provisional application No. 61/075,965, filed on Jun. 26, 2008, provisional application No. 60/972,663, filed on Sep. 14, 2007, provisional application No. 61/159,113, filed on Mar. 11, 2009, provisional application No. 61/310,407, filed on Mar. 4, 2010.

(51) Int. Cl.
    *A61K 25/12* (2006.01)
(52) U.S. Cl. .................................. 424/423; 424/93.7
(58) Field of Classification Search ........................ None
    See application file for complete search history.

(56) References Cited

U.S. PATENT DOCUMENTS

| 5,707,684 | A | 1/1998 | Hayes et al. |
| 7,105,199 | B2 | 9/2006 | Blinn et al. |
| 7,431,959 | B1 | 10/2008 | Dehnad |
| 2002/0017455 | A1 | 2/2002 | Kirkpatrick et al. |
| 2002/0115208 | A1 | 8/2002 | Mitchell et al. |
| 2007/0029500 | A1 | 2/2007 | Coulombe et al. |
| 2007/0148161 | A1* | 6/2007 | Delmotte ............... 424/94.64 |
| 2009/0017438 | A1* | 1/2009 | Roy et al. ................ 435/1.1 |
| 2009/0024229 | A1* | 1/2009 | Chen et al. .............. 623/23.73 |

OTHER PUBLICATIONS

Loh "Plasma surface modification in biomedical applications." Med Device technol. Jan. 1999-FEbl 10(1):24-30.*
Yamada et al. "Materials Processing by gas cluster ion beams". Materials Science and Engineering R 34 (2001) 231-295.*
International Preliminary Report on Patentability, Date of Report Sep. 13, 2011, International Application No. PCT/US2010/026984, International Filing Date: Mar. 11, 2010.
Ito, Y. Surface micropatterning to regulate cell functions. Biomaterials (1999), vol. 20, pp. 2333-2342.
Castner, D.G. et al. Biomedical surface science: Foundations to frontiers. Surface Science (2002), vol. 500, pp. 28-60.
Loh, J. H. Plasma surface modification in biomedical applications. Med Device Technol. (1999) vol. 10(1), pp. 24-30.
Yamada, I. et al. Materials processing by gas cluster ion beams. Materials Science and Engineering (2001) vol. 34, pp. 231-295.
International Search Report dated May 12, 2010 for PCT/US10/26980. Applicant: Exogenesis Corporation.
International Search Report dated May 12, 2010 for PCT/US10/26984. Applicant: Exogenesis Corporation.

* cited by examiner

*Primary Examiner* — Robert A Wax
*Assistant Examiner* — Danah Al-Awadi
(74) *Attorney, Agent, or Firm* — Burns & Levinson LLP; Jerry Cohen; David W Gomes

(57) ABSTRACT

The invention provides methods for surgical grafting of a tissue. The method comprises the steps of explanting a graft tissue from a donor, irradiating at least a first portion of the graft tissue with an ion beam, and surgically grafting the graft tissue into a recipient.

19 Claims, 7 Drawing Sheets

METHOD FOR MODIFYING THE WETTABILITY AND/OR OTHER BIOCOMPATIBILITY CHARACTERISTICS OF A SURFACE OF A BIOLOGICAL MATERIAL BY THE APPLICATION OF GAS CLUSTER ION BEAM TECHNOLOGY AND BIOLOGICAL MATERIALS MADE THEREBY

CROSS REFERENCE TO RELATED APPLICATIONS

This application is a continuation-in-part of co-pending U.S. patent application Ser. No. 12/210,018, filed Sep. 12, 2008, entitled "Method and System for Modifying the Wettability Characteristics of a Surface of a Medical Device by the Application of Gas Cluster Ion Beam Technology and Medical Devices Made Thereby", which in turn claims priority of U.S. Provisional Patent Application No. 61/075,965 filed Jun. 26, 2008 and entitled "Method and System for Modifying the Wettability Characteristics of a Surface of a Medical Device by the Application of Gas Cluster Ion Beam Technology and Medical Devices Made Thereby", and of U.S. Provisional Patent Application No. 60/972,663 filed Sep. 14, 2007 and entitled "Method and System for Modifying the Wettability Characteristics of a Surface of a Medical Device by the Application of Gas Cluster Ion Beam Technology and Medical Devices Made Thereby", all of which are hereby incorporated by reference in their entirety.

This application also claims priority of U.S. provisional application Ser. No. 61/159,113 entitled "Method for Modifying the Wettability and other Biocompatability Characteristics of a surface of a Biological Material by the Application of Gas Cluster Ion Beam Technology and Biological Materials Made Thereby", filed Mar. 11, 2009, and of U.S. provisional application Ser. No. 61/310,407, entitled "Gas Cluster Ion Beam Surface Modification of SLA Titanium Enhances Osteoblast Proliferation and Bone Formation in vitro", filed Mar. 4, 2010, both of which are incorporated herein by reference in their entirety.

FIELD OF THE INVENTION

This invention relates generally to biological materials intended for implant into a mammal and, more particularly to methods using ion beam technology, preferably gas cluster ion beam technology for modifying the wettability and/or for improving the capability of the modified biological materials to 1) act as a host for cell attachment on a surface thereof; 2) to promote cell proliferation on a surface thereof or within the material; 3) to promote cell penetration through and beneath such surfaces, and/or; 4) to promote subsequent new tissue formation.

BACKGROUND OF THE INVENTION

Gas cluster ion beam (GCIB) irradiation has been used for nano-scale modification of surfaces. In the co-pending, commonly held U.S. patent application Ser. No. 12/210,018, "Method and System for Modifying the Wettability Characteristics of a Surface of a Medical Device by the Application of Gas Cluster Ion Beam Technology and Medical Devices Made Thereby", GCIB has been shown to modify the hydrophilic properties of non-biological material surfaces. GCIB processing has been well documented in the manufacturing of semiconductor devices and thin films. However, its potential uses for modifying surfaces of biological materials including tissues of the musculoskeletal system (e.g. bone, ligaments, tendons, rotator cuff, cartilage and such like), as well as for modification of other connective tissues such as epithelial tissue and endothelial tissue within major mammalian and avian organ systems are hitherto unknown. The physical modifications that GCIB processing produces on a ligament surface with respect to its capability to act as a host structure for cell attachment is hitherto unknown. It is generally known that anchorage dependent cells such as fibroblasts and osteoblasts benefit from hydrophilic surfaces to attach, grow, or differentiate well and they also prefer charged surfaces. With respect to hydrophilicity, droplet contact angle may be used as a measure of wettability, with decreasing contact angle measurements generally implying a more hydrophilic surface. Many methods have previously been employed to increase hydrophilicity or alter charge on non-biological surfaces, such as sandblasting, acid etching, plasma spraying of coatings, $CO_2$ laser smoothing and various forms of cleaning, including mechanical, ultrasonic, plasma, and chemical cleaning techniques. Other approaches have included the addition of surfactants or the application of films or coatings having different wettability characteristics. The preparation of surfaces of biological materials by GCIB irradiation for enhanced cellular attachment either through increasing the hydrophilicity of a surface or by modifying the surface charge state or surface chemistry, or by other mechanisms has not been previously demonstrated.

Beams of energetic conventional ions, accelerated electrically charged atoms or molecules, are widely utilized to form semiconductor device junctions, to modify surfaces by sputtering, and to modify the properties of thin films. Unlike conventional ions, gas cluster ions are formed from clusters of large numbers (having a typical distribution of several hundreds to several thousands with a mean value of a few thousand) of weakly bound atoms or molecules of materials that are gaseous under conditions of standard temperature and pressure (commonly oxygen, nitrogen, or an inert gas such as argon, for example, but any condensable gas can be used to generate gas cluster ions) with each cluster ion sharing one or more electrical charges, and which are accelerated together through high voltages (on the order of from about 3 kV to about 70 kV or more) to have high total energies. After gas cluster ions have been formed and accelerated, their charge states may be altered or become altered (even neutralized), and they may fragment into smaller cluster ions and/or neutralized smaller clusters, but they tend to retain the relatively high total energies that result from having previously been accelerated through high voltages. Gas cluster ion beams have been used to process surfaces of non-biological materials for purposes of cleaning, etching, smoothing, film growth, and the like. They are well known for their smoothing effects on most solid material surfaces and have been employed for smoothing materials such as diamond, silicon, and metals. Because of the large number of atoms or molecules in each gas cluster ion, and because they are weakly bound, their effect upon striking a surface is very shallow, unlike the effect of conventional (monomer or molecular) ions. The cluster is disrupted at impact and each atom or molecule then carries only a relatively few eV of energy compared to the total energy of the accelerated cluster. Instantaneous temperatures and pressures can be very high at gas cluster ion impact sites, and a variety of surface chemistry, etching, and other effects can occur. Surface chemistry may be modified by GCIB irradiation (for example) by exposing surface bonds (thus modifying surface charge states) and/or by incorporation of reactive atoms or molecules from the gas cluster ions into the surface (by using gas cluster ions comprising reactive atoms or molecules such as oxygen, nitrogen, carbon, etc.) However, these effects are very superficial, extending, at most, some tens of Angstroms beneath the impact site and accordingly there is no significant damage to any material located deeper below the superficial surface impact site. As used herein, the terms "GCIB", "gas cluster ion beam" and "gas cluster ion" are intended to encompass accelerated beams and ions that have had all or a portion of their charge states modified (including neutralized) following their acceleration. The terms "GCIB" and "gas cluster ion beam" are intended to encompass all beams that comprise accelerated gas clusters even though they may also comprise non-clustered particles. GCIB is a preferred ion beam for the present invention because of the fact that penetration is very shallow, with negligible damage or modification deeper than a few tens of Angstroms (a few nanometers).

In one aspect the invention provides methods for increasing the wettability and/or altering the chemistry or charge state and/or modifying other physical characteristics of a surface of a biological material by the application of gas cluster ion beam technology.

In a further aspect the invention provides methods for preparing a surface of a biological material for attachment, proliferation, migration, etc. of new cellular growth, by the application of gas cluster ion beam technology, and optionally, for the stimulation of the new cells to differentiate into tissue such as bone, fibrous connective tissue, epithelium, endothelium or the like.

In yet another aspect the invention provides methods for increasing the wettability of a portion of a surface of a biological material and/or for preparing a surface of the biological material for attachment, proliferation, migration, etc. of new cellular growth, in a controlled pattern, by the application of gas cluster ion beam technology.

In a still further aspect the invention provides a surgically implantable biological material that has a surface or surface portion with increased hydrophilicity and/or that has a surface with an enhanced capability for cell penetration and/or to act as a host for new cellular attachment, growth, and differentiation, by the application of gas cluster ion beam technology, and optionally, for the stimulation of the new cells to differentiate into tissue such as bone, fibrous connective tissue, epithelium, endothelium or the like.

In another aspect the invention is provides a biological material for surgical implantation and/or graft as well as a method for preparation and surgical implantation of a biological material graft incorporating a specific cellular material in the graft, and optionally for stimulating the specific cellular material to differentiate into tissue such as bone, fibrous connective tissue, epithelium, endothelium, or the like.

SUMMARY OF THE INVENTION

The foregoing aspects as well as further and other aspects and advantages of the present invention are achieved by the invention described hereinbelow.

The present invention applies gas cluster ion beam (GCIB) processing of a surface or a portion of a surface of a biological material to modify its surface properties such as the hydrophilicity or the degree of wettability of the surface and/or to improve the suitability of the surface or a portion of the surface to act as a host for new cellular growth and/or attachment to biological materials including tissues of the musculoskeletal system, e.g. bone, ligaments, tendons, rotator cuff, cartilage and the like. Through the use of masking techniques or by controlling the incidence of the GCIB onto the surface or by other means of controlling the spatial extent of the GCIB processing, the surface characteristics may be modified in a controlled pattern with desired regions modified and other regions unmodified. Thus, cellular attachment to the biological material (when surgically implanted) may be facilitated at the desired regions, without encouraging cellular attachment at regions where it is not appropriate to a successful surgical outcome.

The inventors have processed surfaces of tissues of the musculoskeletal system e.g. bone and ligament (in both natural and decellularized states) with GCIB techniques and have found that certain types of GCIB processing result in increasing the hydrophilicity of the surfaces of the biological materials and in improving the suitability of the surfaces for new cellular growth and attachment. The examples given herein are structural tissues but the invention is not limited to structural tissue.

For producing patterned surface variations, the GCIB processing may be controlled using masks or beam writing techniques, or various other means for controlling the exposure of the workpiece surfaces to GCIB processing in such a way as to restrict processing to certain regions of the surface or to produce differing types of GCIB processing in differing regions of the workpiece. Masks employed may be mechanical masks that shadow portions of the workpiece from GCIB processing. The achievement of patterned surface variations is not limited to the use of mechanical masks.

The instant invention provides a method for surgical grafting of a tissue. The method comprises the steps of explanting a graft tissue from a donor, irradiating at least a first portion of the graft tissue with an ion beam, and surgically grafting the graft tissue into a recipient.

The instant invention also provides another method for surgical grafting, the method comprises the steps of explanting a graft tissue from a donor, decellularizing at least a first portion of the graft tissue, lyophilizing at least a second portion of the first portion of the graft tissue, irradiating at least a third portion of the second portion of the graft tissue, and surgically grafting the graft tissue into a recipient. The method further comprises optional steps of storing the graft tissue for future use, transporting the graft tissue to a remote site for surgical grafting, seeding cells onto at least a surface of the at least a third portion of the graft tissue, and allowing a desired degree of attachment and proliferation of the cells onto or into the graft tissue.

For a better understanding of the present invention, together with other and further objects thereof, reference is made to the accompanying drawings and detailed description and its scope will be pointed out in the appended claims.

DETAILED DESCRIPTION OF INVENTION

Figure 1:
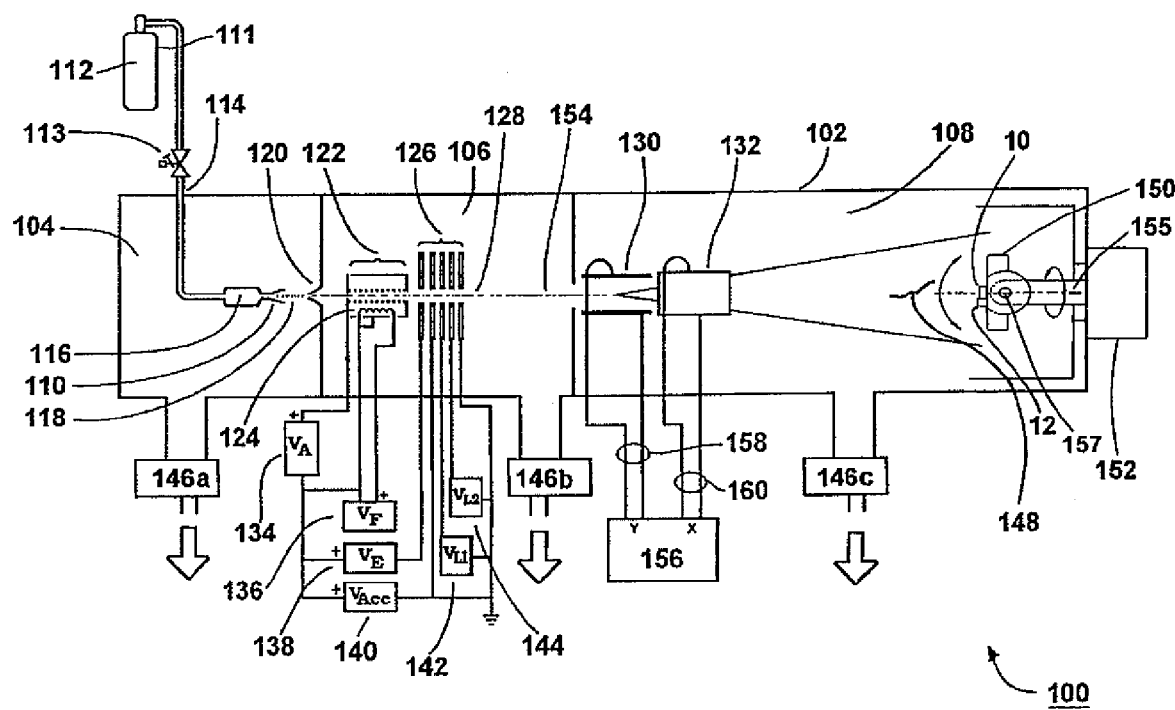
FIG. 1 is a schematic view of a gas cluster ion beam processing system of a type known in the GCIB art and suitable for practicing the invention.

Reference is made to FIG. 1 of the drawings, which shows a typical gas cluster ion beam (GCIB) processor 100 of a type known in prior art for surface processing. Although not limited to the specific components described herein, the processor 100 is made up of a vacuum vessel 102 which is divided into three communicating chambers, a source chamber 104, an ionization/acceleration chamber 106, and a processing chamber 108 which includes therein a workpiece holder 150 capable of positioning a workpiece 10 for processing by a gas cluster ion beam.

During use, the three chambers are evacuated to suitable operating pressures by vacuum pumping systems 146a, 146b, and 146c, respectively. A condensable source gas 112 (for example argon or $N_2$) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, most consisting of from a few hundred to several thousand (or even tens of thousands) weakly bound atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to inert gases (such as argon), nitrogen, carbon dioxide, and oxygen.

After the supersonic gas jet 118 containing gas clusters has been formed, the clusters are ionized in an ionizer 122. The ionizer 122 may be an electron impact ionizer that produces thermoelectrons from one or more incandescent filaments 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions with an acceleration potential (typically from 1 kV to as much as several tens of kV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{Acc}$ to bias a high voltage electrode with respect to the ionizer 122 so as to result in a total GCIB acceleration potential equal to $V_{Acc}$ volts (V). One or more lens power supplies (142 and 144, for example) may be provided to bias high voltage electrodes with potentials ($V_{L1}$ and $V_{L2}$ for example) to focus the GCIB 128.

A workpiece 10 to be processed by the GCIB processor 100 is held on a workpiece holder 150, disposed in the path of the GCIB 128. An optional retainer 12 that may be a clip or clamp or other retaining item may be employed to retain the workpiece 10 in an attached position on the workpiece holder 150. In order for uniform processing of the workpiece 10 to take place, the workpiece holder 150 is designed in a manner set forth below to appropriately manipulate workpiece 10, as may be required for uniform processing.

Figure 2:
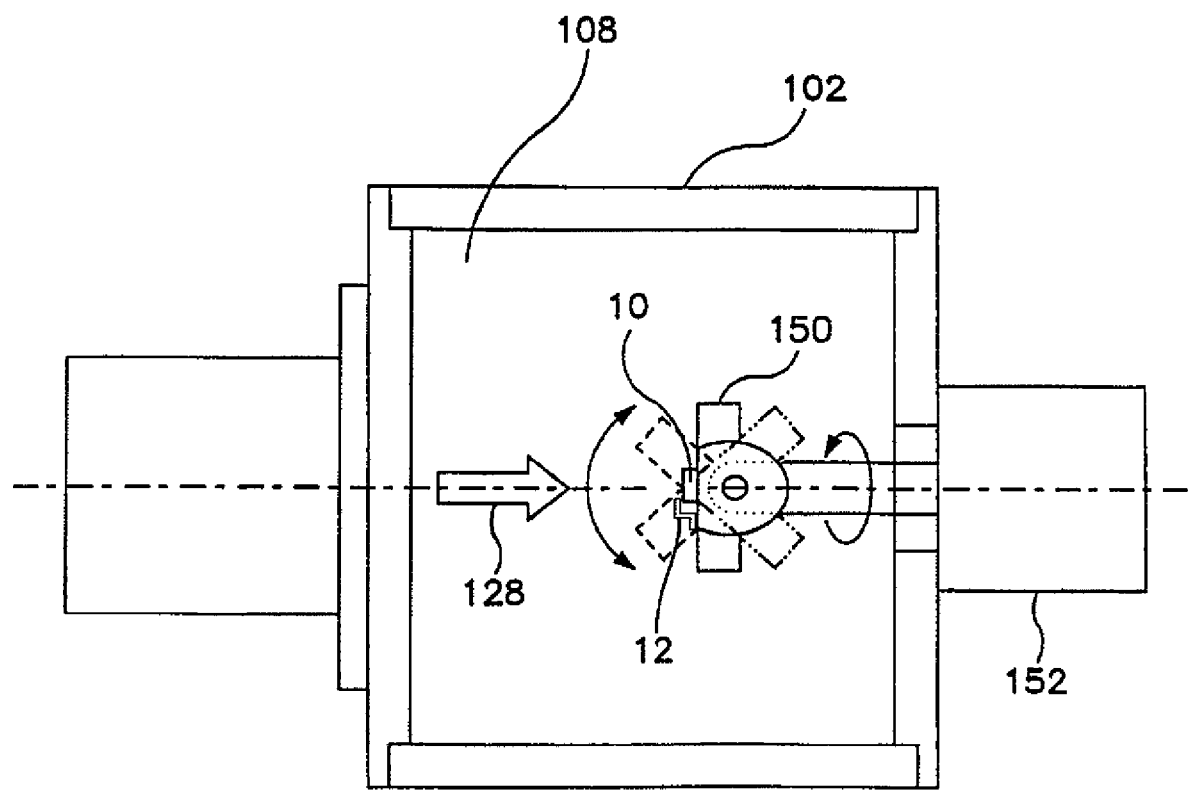
FIG. 2 is an enlarged view of a portion of the gas cluster ion beam processing system showing the workpiece holder.

Referring also to FIG. 2, any workpiece surfaces that are non-planar, that is may be of a spherical or cup-like, rounded, irregular, or other un-flat configuration (as may be encountered among biological materials), may be oriented within a range of angles with respect to the beam incidence to obtain optimal GCIB processing of the workpiece surfaces. This employs a workpiece holder 150 with the ability to be fully articulated for orienting all non-planar surfaces to be processed in suitable alignment with the GCIB to provide processing optimization and uniformity. More specifically, when the workpiece 10 being processed is non-planar, the workpiece holder 150 may be rotated and articulated by a mechanism 152 located at the end of the GCIB processor 100. The articulation/rotation mechanism 152 preferably permits 360 degrees of device rotation about longitudinal axis 155 (which may be coaxial with the initial trajectory 154 of the GCIB 128) and sufficient articulation about an axis 157 perpendicular to axis 155 to maintain the workpiece surface to within a desired range of beam incidence.

Under certain conditions, depending upon the size of the workpiece 10, a scanning system may be desirable to produce uniform irradiation of a large workpiece. Although not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the workpiece 10.

When beam scanning over an extended region is not desired, processing is generally confined to a region that is defined by the diameter of the beam. The diameter of the beam at the surface of the workpiece can be set by selecting the voltages ($V_{L1}$ and/or $V_{L2}$) of one or more lens power supplies (142 and 144 shown for example) to provide the desired beam diameter at the workpiece. Although not specifically shown, in FIGS. 1 and 2, such prior art GCIB processing systems typically employ sensors and circuits for measuring and controlling the GCIB parameters (as for example acceleration potential, beam current, beam focus, gas flow, beam dose applied to the workpiece, workpiece manipulation, etc.) important to processing and also employ additional controls and automation for automatic processing and processing recipe management, selection, and control.

Although FIGS. 1 and 2 show a workpiece holder and manipulator suitable for holding and manipulating certain types of planar and simply shaped non-planar workpieces, it will be understood by those familiar with the prior art that other types of simpler and more complex holders and manipulators are known. For example, U.S. Pat. No. 6,676,989 granted to Kirkpatrick et al. teaches a holder and manipulator optimized for processing tubular or cylindrical workpieces such as vascular stents. Manipulators for exposing multiple surfaces of biological materials to GCIB irradiation will be known to those skilled in the art and/or may readily be constructed using no more than ordinary skill.

Tests were performed to determine the effect of GCIB irradiation on the droplet contact angle (as a measure of hydrophilicity) for biological tissues. Young porcine knees were used to harvest medial collateral ligaments (MCL) and lateral collateral ligaments (LCL) as well as femur shafts. The ligaments were carefully dissected from other loose tissues, rinsed in phosphate buffered saline (PBS) and cut into pieces of approximately 1 cm length by their natural width of approximately 5 mm. Bone shafts were cut to cylinders approximately 2 cm in length and further cut longitudinally down the shaft to semi-circle shaped pieces. The pieces were cleaned of periosteum by pulling it off using forceps and were then rinsed in PBS. Subsequent processing of both the bone and ligament tissue samples (including controls) was identical. Tissues were stored in PBS overnight. Then the tissue samples (both bone and ligament) were removed from PBS and individually introduced into a GCIB processing system's processing chamber. The processing chamber was evacuated to a rough vacuum of approximately 100 mtorr (evacuation time for achieving rough vacuum was approximately 30 minutes for the bone samples and approximately 2 minutes for the ligament samples.) After achieving rough vacuum, the samples were subsequently introduced to high vacuum and exposed to high vacuum (approximately $6 \times 10^{-5}$ torr.) Test samples of both bone and ligament tissues were then treated in high vacuum by GCIB irradiation. Control samples were not irradiated but were subjected to the same vacuum conditions and durations. GCIB irradiation consisted of administering a surface dose of $5 \times 10^{14}$ argon clusters per cm$^2$ at 30 kV acceleration potential to the irradiated surfaces. The irradiation time and corresponding high vacuum exposure duration was approximately 3 minutes and 20 seconds for both the bone and ligament tissue samples.

Following GCIB irradiation and/or vacuum exposure, the tissue samples were allowed to air dry over night in a biosafety cabinet.

Wettability of the samples was examined by using a Drop Shape Analysis System (Krüss GmbH, Hamburg, Germany, model DSA-10, with Krüss DSA1 version 1.8 analysis software) was used to determine surface contact angles for water droplets on the tissue samples. Identical measurements were made for the bone and ligament tissues, both the irradiated samples and the unirradiated control samples. For each measurement, data was obtained 5 seconds after placing a 3 microliter droplet of deionized water on each of the surfaces (ligament and bone, both irradiated and unirradiated controls.) All measurements were performed under ambient conditions and each analysis was performed in triplicate (three tests on each single sample.)

Results showed an increase of hydrophilicity as measured by decreased contact angle for the ligament and bone samples that were GCIB irradiated, as compared to the unirradiated control samples.

Figure 3:
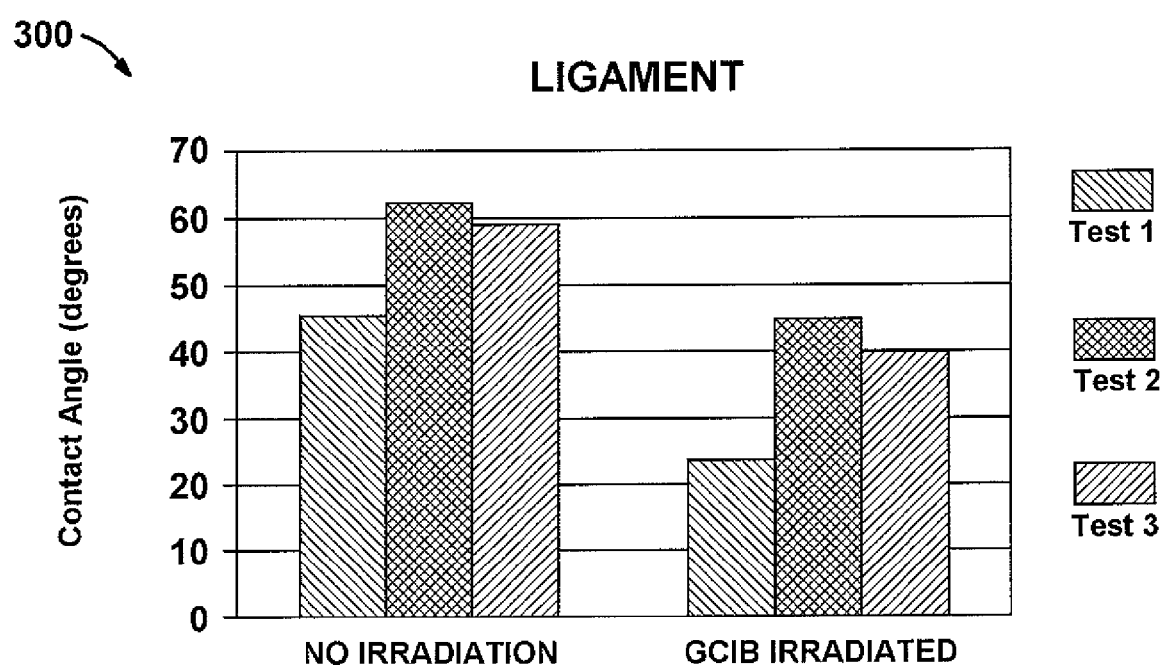
FIG. 3 is a chart showing a measured reduction of droplet contact angle resulting from GCIB irradiation of ligament tissue according to an embodiment of the invention.

FIG. 3 is a chart 300 showing droplet surface contact angle test results for each of three measurements on ligament tissue samples, for both GCIB irradiated and the unirradiated control samples. Droplet contact angle measurements using deionized water on the ligament tissues show an increased hydrophilic surface on the ligament tissue in response to GCIB treatment. Droplet contact angles decreased from an average of 55.59+/−9.03 in the unirradiated control ligament to 36.09+/−10.93 in the GCIB irradiated samples (statistical significance of the change, p<0.004).

Figure 4:
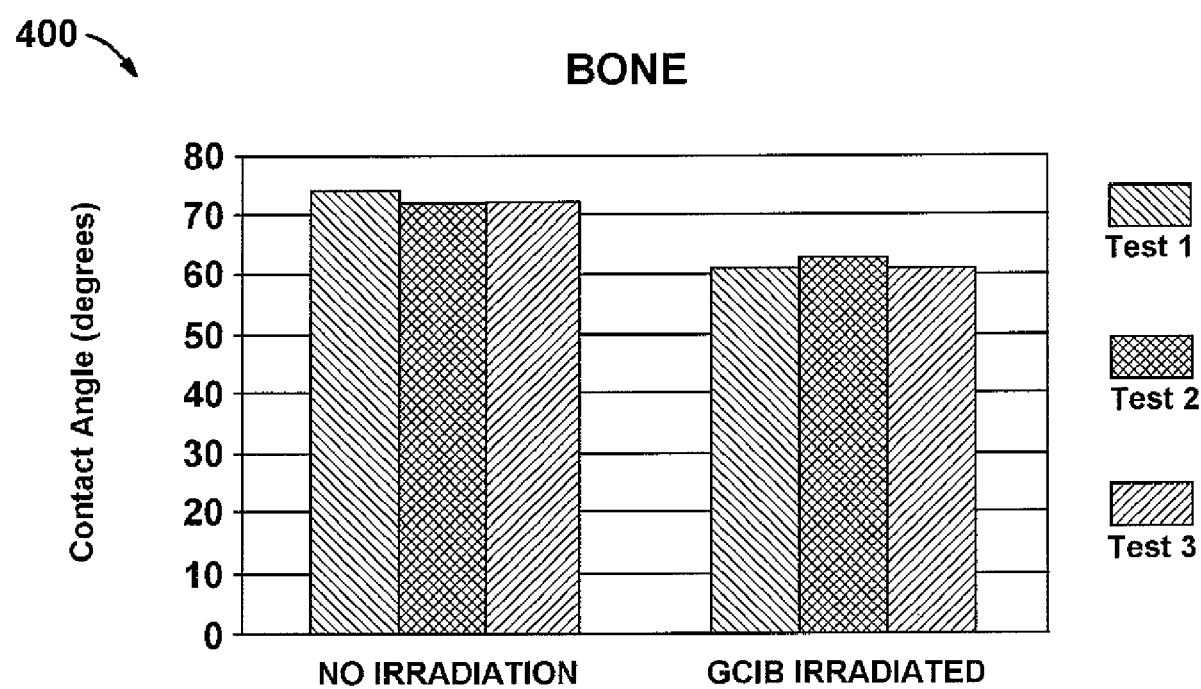
FIG. 4 is a chart showing a measured reduction of droplet contact angle resulting from GCIB irradiation of bone tissue according to an embodiment of the invention.

FIG. 4 is a chart 400 showing droplet surface contact angle test results for each of three measurements on bone tissue samples, for both GCIB irradiated and the unirradiated control samples. Droplet contact angle measurements using deionized water on the bone tissues show an increased hydrophilic surface on the bone tissue in response to GCIB treatment. Droplet contact angles decreased from an average of 72.86+/−1.47 in the unirradiated control bone to 61.42+/−1.06 in the GCIB irradiated samples (statistical significance of the change, p<0.015).

Because GCIB treatment of biological surfaces resulted in a more hydrophilic surface, additional tests were done to show that GCIB treatment of decellularized ligaments results in a surface that can be better re-cellularized by (for example) fibroblast cells. Pieces of porcine anterior cruciate ligament (ACL) were used to harvest fibroblasts using a published explant method (Ross S M, Joshi R, and Frank C B; "Establishment and comparison of fibroblast cell lines from the medial collateral and anterior cruciate ligaments of the rabbit" *In Vitro Cell Dev Biol* 1990; 26:579-84.) Freshly isolated LCL and MCL from young porcine knees were then decellularized using the technique of an established method (Woods T, Gratzer P F; "Effectiveness of three extraction techniques in the development of a decellularized bone-anterior cruciate ligament-bone graft", *Biomaterials* 2005, 26:7339-7349.)

Except for GCIB irradiation, subsequent processing of the ligament tissue samples (both the test samples and the controls) was identical. Decellularized tissues were stored in PBS overnight. Then the decellularized tissue samples were removed from PBS and individually introduced into a GCIB processing system's processing chamber. The processing chamber was evacuated to a rough vacuum of approximately 100 mtorr (evacuation time for achieving rough vacuum was approximately 2 minutes for the ligament samples.) After achieving rough vacuum, the samples were subsequently introduced to high vacuum and exposed to high vacuum (approximately $6 \times 10^{-5}$ torr.) Test samples of decellularized ligament tissues were then treated in high vacuum by GCIB irradiation. Control samples were not irradiated, but were subjected to the same vacuum conditions and durations. GCIB irradiation consisted of administering a surface dose of $5 \times 10^{14}$ argon clusters per cm$^2$ at 30 kV acceleration potential to the irradiated surfaces. The irradiation time and corresponding high vacuum exposure duration was approximately 3 minutes and 20 seconds for both the decellularized ligament tissue samples (irradiated and control).

Approximately $2 \times 10^5$ fibroblast cells suspended in Sigma E1270 extracellular matrix (ECM) were placed on either side of the ligament samples (to seed the decellularized and irradiated tissue with new cells) and placed in tubes containing appropriate cell growth medium (Dulbecco's Modified Eagle Medium+10% fetal bovine serum+1% Penicillin/Streptomycin Antibiotic (supplied by Invitrogen)) and allowed to grow for 18 days with regular medium change every 3 days. Ligament specimens were then fixed in formalin, processed for histology and stained with hematoxylin and eosin. Microscopic inspection of the ligaments revealed a much enhanced cellular attachment and proliferation on the ligament samples receiving GCIB treatment as compared to those controls without GCIB treatment.

Figure 5:
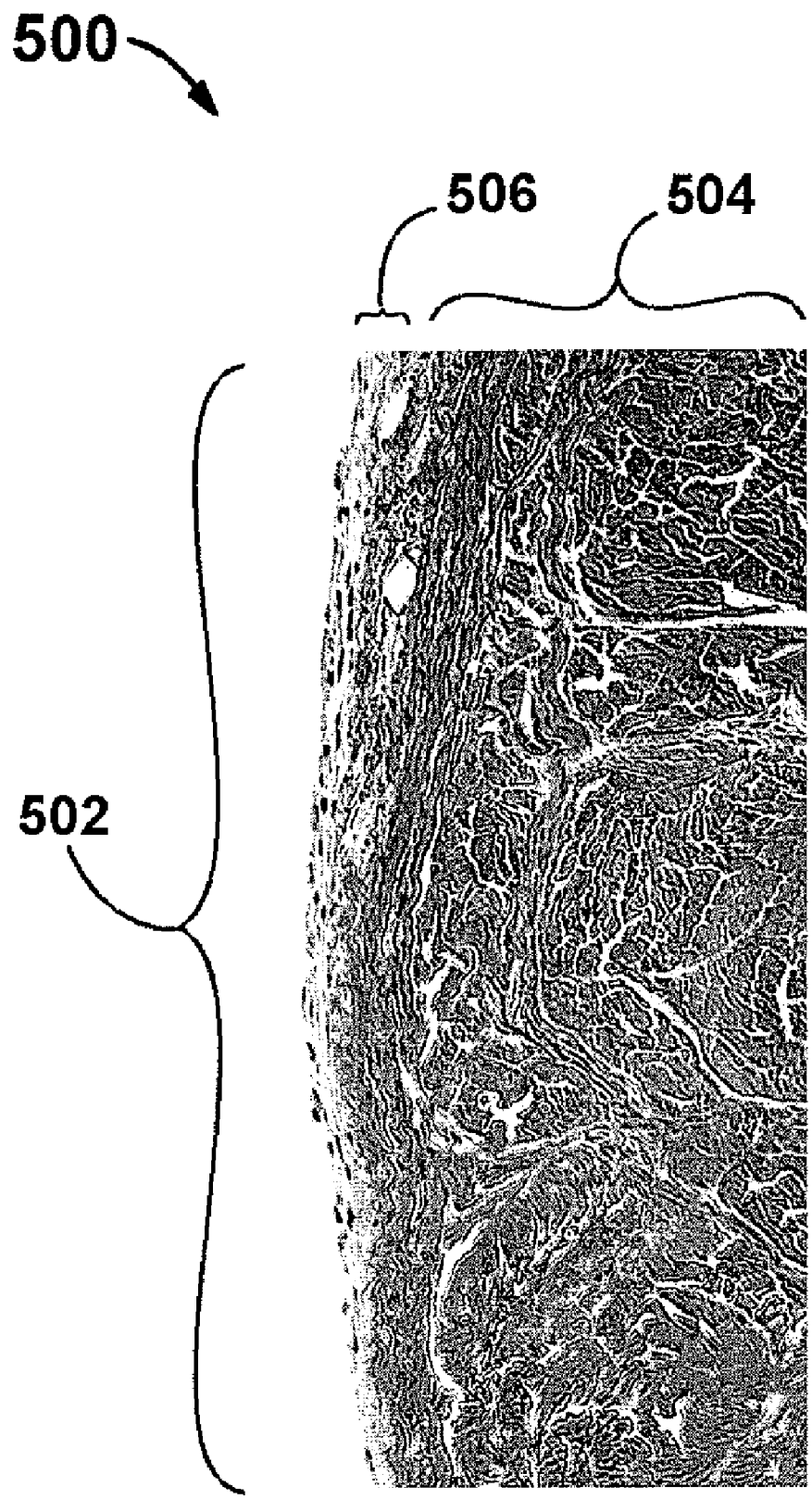
FIG. 5 is a micrograph showing cell growth on a control ligament sample.

FIG. 5 shows a micrograph 500 showing a surface region 502 of an unirradiated control sample of decellularized porcine ligament tissue 504 processed as described above including vacuum exposure, but without GCIB irradiation. A 1- to 2-cell layer 506 of newly grown fibroblast cells is seen attached to the underlying ligament tissue 504.

Figure 6:
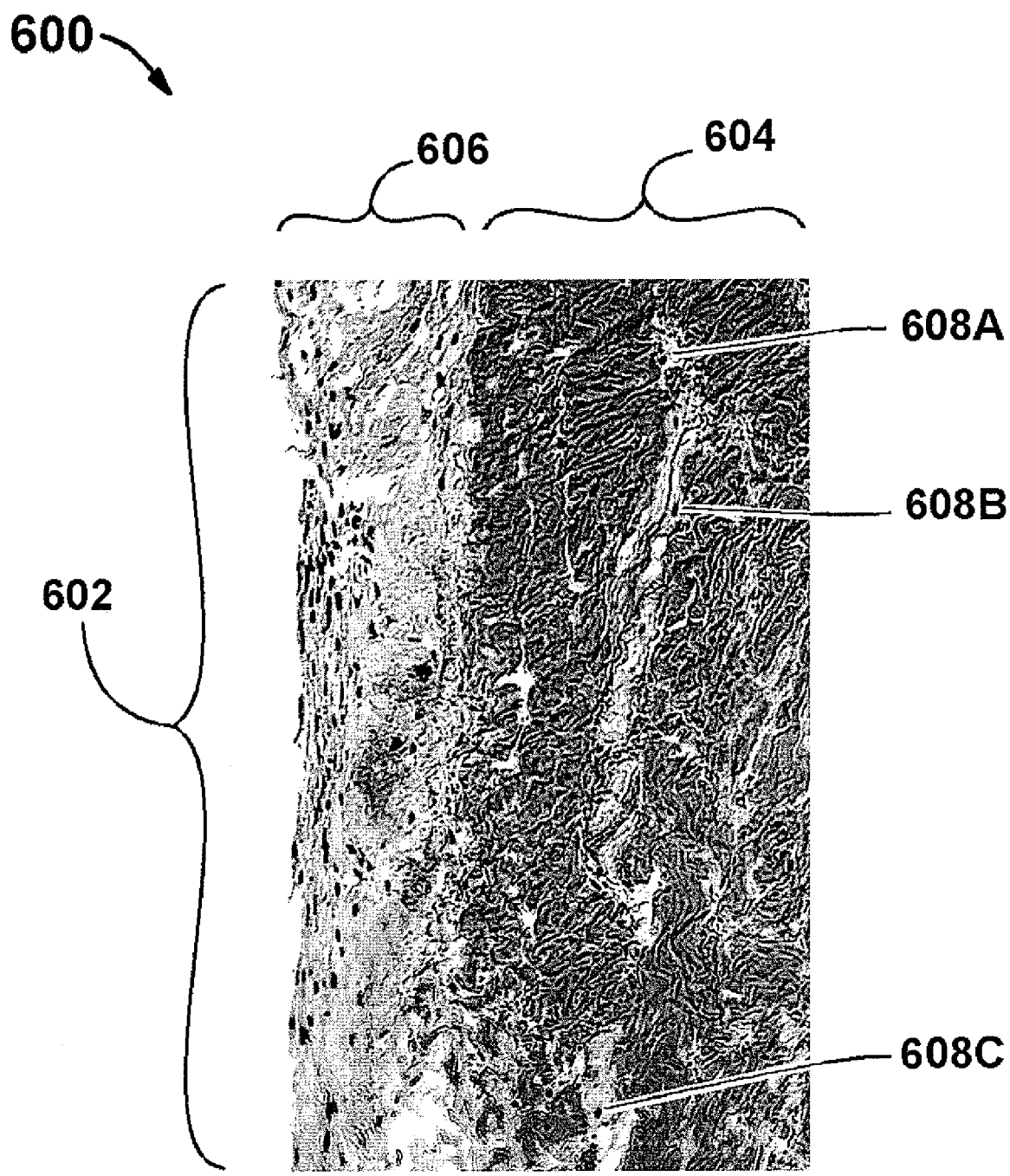
FIG. 6 is a micrograph showing enhanced cell growth on a ligament sample processed according to an embodiment of the invention.

FIG. 6 shows a micrograph 600 showing a surface region 602 of a GCIB irradiated sample of decellularized porcine ligament tissue 604 processed as described above, including both vacuum exposure and GCIB irradiation. Magnification in FIG. 6 is the same as for that in FIG. 5. In FIG. 6, a 3- to 7-cell layer 606 of newly grown fibroblast cells is seen attached to the underlying ligament tissue 604 at the irradiated surface. Furthermore, numerous new fibroblast cells (608A, 608B, and 608C for examples) are seen embedded much deeper into the decellularized ligament tissue. The newly grown fibroblast cells, in addition to having proliferated on the GCIB irradiated surface have begun migrating into the ligament.

These results indicate that the GCIB irradiation of the surface of the decellularized ligament has created a more favorable environment for attachment, growth, or proliferation of the fibroblast cells on the outer surface such that there is more vigorous surface growth and increased migration into the ligament. The migration of cells into the ligament is an important advance in the field of ligament tissue engineering for surgical implant. GCIB treatment of biological materials may result in significantly improved clinical outcomes for surgical procedures (as for example an ACL reconstruction). Hitherto, ACL reconstructive surgery (for example) has limited success over time due, in part, to relatively poor integration of transplanted ligament or tendon tissue into the body. GCIB treated ligaments or tendons will integrate more rapidly and form a more tightly bound integration that extends the benefits achieved with traditional ACL reconstructive surgical techniques.

It is commonly known that primary culture cells de-differentiate while growing in vitro. Various growth and mitogenic factors may be added in culture to maintain the original genotype and morphology of the cells. Primary human osteoblasts were grown in tissue culture plates with no additional growth or mitogenic factors other than found in the (Invitrogen) Dulbecco's Modified Eagle Medium+10% fetal bovine serum+1% penicillin/streptomycin antibiotic for two to four passages. Osteoblasts in passage two to four were seeded onto titanium either in control state or that had been irradiated by GCIB at $5 \times 10^{14}$ argon clusters per $cm^2$ and the osteoblasts were allowed to attach and proliferate for 1, 7, or 10 days. Following this time, RNA was extracted from the cells using the TRIzol method (Invitrogen). Following RNA quantification by UV-spectrometry analysis, equal quantities of RNA (1 micro-g) were reverse transcribed into cDNA using the iScript cDNA synthesis kit (Bio-Rad). 100 pg of the resulting cDNA was subjected to real-time polymerase chain reaction (Real Time PCR) for expression analysis of various genes known to be involved in osteogenesis including alkaline phosphatase—liver, bone, kidney (ALPL) known to be involved during bone formation and mineralization, and bone gamma-carboxyglutamate (gla) protein (BGLAP) known to produce a bone protein called Osteocalcin, and corrected for the house keeping gene GAPDH. The analysis was performed on a StepOne system with TaqMan Gene Expression Master Mix and gene specific primers (all from Applied Biosystems), n=3 per condition and time point. The fold change relative to control results were obtained using the $\Delta\Delta C_T$ method. We have shown that osteoblast cells grown on the argon GCIB-treated titanium lead to 3.41 fold increase in ALPL and 2.66 fold increase in BGLAP as compared to non-GCIB-treated titanium at day 10 (statistical significance of the change, $p<0.05$) indicating that the osteoblast cells are undergoing differentiation that will lead towards osteogenesis. Thus the GCIB treatment of a surface, alone, induces differentiation of cells proliferating on the GCIB treated surface.

In the case of biological materials, it is often desirable that only preselected portions of the materials should be processed by GCIB irradiation, while other portions are best not irradiated. In such situations, controlling the GCIB cross-sectional area and controlling the scanning and/or deflecting of the GCIB to limit the extent of its irradiation to only the desired areas may control exposure of selected portions of the biological materials to GCIB. Alternatively, conventional masking technology may be used to control the mask surface areas of the biological materials for which irradiation is not desired, and to expose surface areas for which irradiation is desired. Subsequently the mask and the biological material exposed through the mask are irradiated with a diffuse or scanned GCIB. Various other methods of limiting the GCIB irradiation to selected regions of a biological material will be known to those skilled in the art and are intended to be encompassed in the invention.

Certain first selected portions of a biological material may be processed performing a first GCIB irradiation upon those selected portions. Additional selected portions of the biological material may further be processed by performing one or more additional processes of GCIB irradiation. The additional GCIB irradiation process(es) may employ different GCIB and vacuum processing conditions, for example different GCIB doses, or different constituent gases in the gas cluster ions, or different beam acceleration potentials (resulting in different ion beam energy and velocity). The additional selected portions may be different portions from the first selected portions or may partially or completely correspond to the first selected portions or may include all of the first selected portions plus additional portions. Such selective processing may be employed to elicit different desired responses in re-cellularization and in subsequent integration into a body after surgical implant or grafting.

Furthermore, any given piece of biological material, may also be uniformly processed by a single GCIB irradiation process and subsequently respond in differing positive ways to the surgical implant process according to the surgical site, application of other medicaments, or other local factors. For example a tendon used for an ACL replacement may be uniformly treated with a single GCIB irradiation process. When surgically implanted, due to local influences, some portions in contact with bone promote enhanced migration, attachment and differentiation of osteoblasts, leading to bone formation promoting integration of the tendon into the anchoring bone, while other cell types are preferentially attracted to other portions of the implanted tendon not in contact with bone. Most importantly, fibroblasts including ligamentous fibroblasts found in the synovial capsule portion (where the graft functions as a replacement ligament) are preferentially attracted to, adhere, and enter the graft, By direct application of appropriate growth and differentiation factors, such as platelet rich plasma (PRP); repulsive guidance molecules (RGMa, RGMb, and/or RGMc); cytokines including macrophage colony stimulatory factor (M-CSF), granulocyte-macrophage colony stimulatory factor (GM-CSF), interleukin-1 and -9 (IL1, IL6), or tumor necrosis factor α (TNFα); members of the transforming growth factors (TGFβ super-family) including TGFβ-1, TGFβ-2, TGFβ-3 and all the bone morphogenic proteins (BMPs), Activin A, growth differentiation factors (GDF), and Nodal; platelet derived growth factors (PDGF-AA, -AB, & -BB); fibroblast growth factors (FGFs); insulin-like growth factors (IGFs); epidermal growth factors (EGFs); or vascular endothelial growth factors (VEGFs); or by the application of demineralized bone powder containing TGFβ or members of that family, the cellular regrowth can be differentiated in favor of a desired tissue type. Alternatively, by applying concentrates in situ, for example, of mesenchymal stem cells from the fat pads found in a joint synovial space, or in the buffy coat layer of bone marrow extracted from the recipient's femur or elsewhere, regrowth of cells that naturally differentiate to the appropriate tissue for the locality is facilitated.

Figure 7:
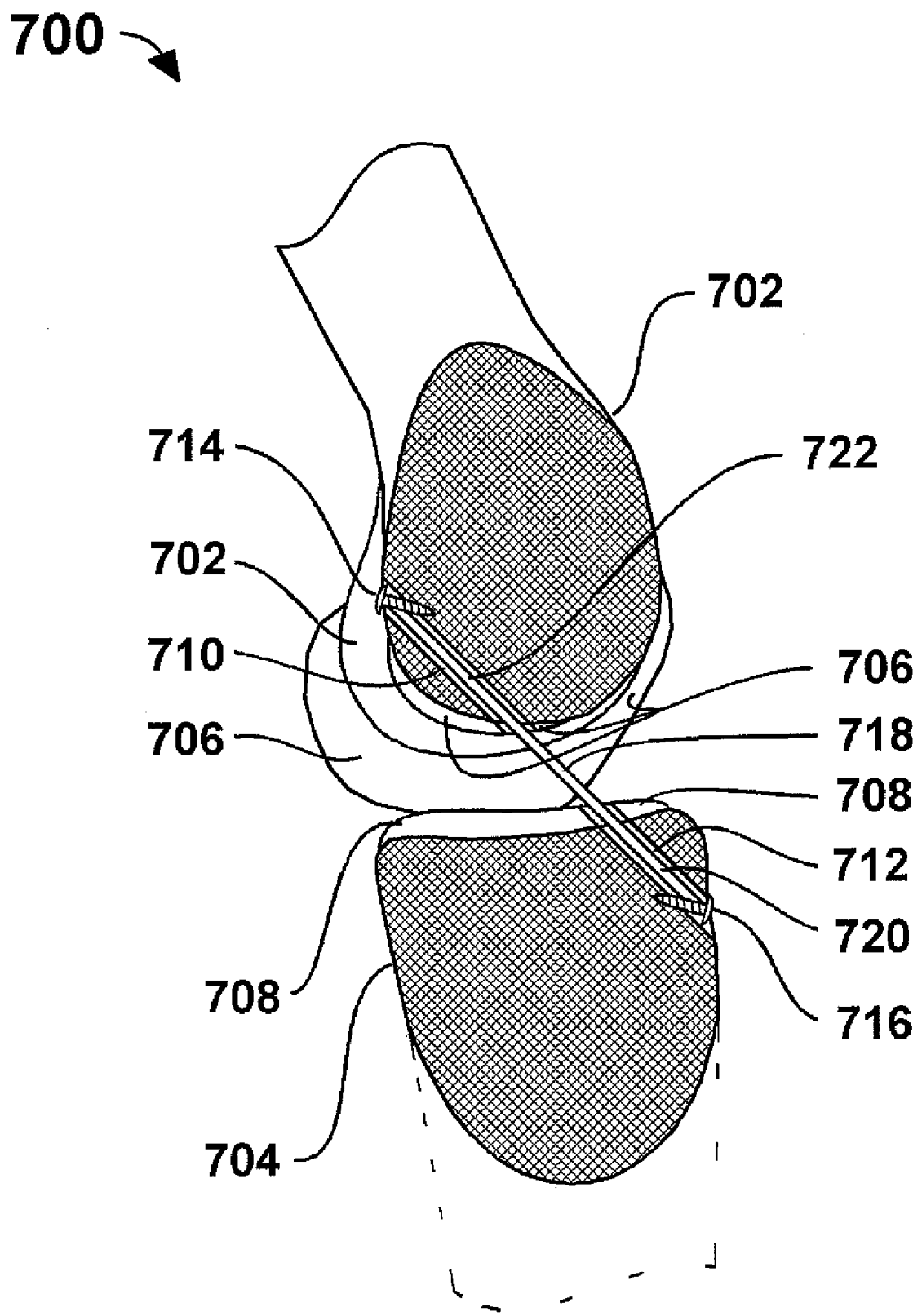
FIG. 7 is a schematic of a knee joint illustrating an exemplary embodiment of beneficial application of the improved biological material of the invention.

FIG. 7 is a schematic 700 of a knee joint illustrating an exemplary embodiment of beneficial application of the improved biological materials of the invention for ligament replacement in an injured joint. The schematic is shown for illustrative purposes and is not necessarily to scale. Rupture of the anterior cruciate ligament (ACL) of a knee joint is an injury often requiring surgical grafting of a replacement for the damaged ACL. A ligament or tendon or a portion thereof may serve as the replacement graft. The graft can be derived from autologous, allogeneic, or xenogeneic tissue. There are a variety of conventional surgical repair techniques. An improved approach uses a decellularized, lyophilized, GCIB irradiated tendon or ligament tissue designated in FIG. 7 as graft 718. Schematic 700 shows a sectional view of a of an ACL replacement graft in a knee joint. The lower end of the femur 702 has femoral cartilage 706. The upper end of the tibia 704 has tibial cartilage 708. Cartilage 706 and cartilage 708 form the articulating contact surfaces of the knee joint. The crosshatched areas of femur 702 and tibia 704 represent, respectively, sectioned (for illustrative purposes only, not surgically sectioned) surfaces of the femur 702 and the tibia 704. For convenience, the section is shown taken through a plane in which the replacement graft 718 lies. Tunnels 710 and 712 are drilled in the femur 702 and the tibia 704 respectively and also penetrate the tibial cartilage 708 and femoral cartilage 706 between the bones. A variety of tunnel configurations may be employed and the configuration shown for tunnels 710 and 712 are only intended as examples. For clarity the patella is not shown and neither is the synovial capsule that encloses the joint and retains the synovial fluid that bathes all the interior surfaces of the joint. The replacement graft 718 of the invention is placed into the tunnels 710 and 712 and is fastened at the femoral end and the tibial end by fasteners 714 and 716 respectively. Any of a variety of fasteners and fixing techniques (including metal and biodegradable polymeric fasteners) may be employed and the fasteners 714 and 716 are only intended to be exemplary. The graft 718 has a femoral inserted portion 722 inserted and retained in the femoral tunnel 710 and has a tibial inserted portion 720 inserted and retained in the tibial tunnel.

In one embodiment, the decellularized, lyophilized, GCIB irradiated tissue of graft 718 is not reconstituted prior to its surgical placement and fastening in the joint. The synovial fluid (not shown) that bathes the joint is in contact with the graft 718 including both the femoral inserted portion 722 and the tibial inserted portion 720. Fibroblasts in the synovial fluid (or existing within remnant fibrils of the damaged and extirpated ACL) contact the graft 718, and attach to and proliferate within the graft 718. These fibroblasts grow and differentiate into appropriate ligamentous fibroblasts and ultimately reconstruct healthy tissue. At the femoral inserted portion 722 and the tibial inserted portion 720 of the graft 718, where the graft contacts the bone of the tunnel 712 in the tibia and the tunnel 710 in the femur the inserted portions 720 and 722 contact bone tissue containing blood and precursors of the bone osteoblasts. Osteoblasts spread on the surfaces of the inserted portions 720 and 722 of the graft 718 and attach, proliferate and differentiate into bone tissue that ultimately completely remodels and replaces graft structure in the inserted portions 720 and 722 of the graft 718.

In another embodiment, prior to surgical placement of the graft 718, the portions of the graft that will become the inserted portions 720 and 722 and/or the portions of the graft that are not to be inserted with bone may be treated with the addition of appropriate growth and differentiation factors such as platelet rich plasma (PRP); repulsive guidance molecules (RGMa, RGMb, and/or RGMc); cytokines including macrophage colony stimulatory factor (M-CSF), granulocyte-macrophage colony stimulatory factor (GM-CSF), interleukin-1 and -9 (IL1, IL6), or tumor necrosis factor α (TNFα); members of the transforming growth factors (TGFβ super-family) including TGFβ-1, TGFβ-2, TGFβ-3 and all the bone morphogenic proteins (BMPs), Activin A, growth differentiation factors (GDF), and Nodal; platelet derived growth factors (PDGF-AA, -AB, & -BB); fibroblast growth factors (FGFs); insulin-like growth factors (IGFs); epidermal growth factors (EGFs); or vascular endothelial growth factors (VEGFs). Alternatively, by applying concentrates in situ, for example, of mesenchymal stem cells from the fat pads found in a joint synovial space, or in the buffy coat layer of bone marrow extracted from the recipient's femur or elsewhere, regrowth within the graft of cells that naturally differentiate to the appropriate tissue for the locality is facilitated, for example promoting differentiation of cells that attach and proliferate in the inserted portions 720 and 722 toward the production of healthy bone.

In still another embodiment, demineralized bone powder comprising bone collagen and other non-mineral components of bone and optionally including TGF-β or members of that family, is inserted into the tunnels 710 and 712, and in contact with the inserted portions 722 and 720 of the graft 718 to promote differentiation of cells that attach and proliferate in the inserted portions 720 and 722 toward the production of healthy bone.

In a further embodiment, stem cells from the fat pads found in the joint synovial space, or in the buffy coat layer of bone marrow extracted from the patients femur or elsewhere are applied in situ to the inserted portions 720 and 722 of the graft 718 to promote differentiation of cells that attach and proliferate in the inserted portions 720 and 722 toward the production of healthy bone.

Although the invention has been described here, for exemplary purposes, in terms of certain materials including bone, ligament and tendon, it is understood that other biological materials are included within the scope of the invention. Although exemplary embodiments have been described in terms of an ACL joint repair, it is understood that a wide variety of other joint and soft tissue grafts benefit from the invention and are intended to be included in the invention. Although an embodiment of the invention has been taught in terms of fresh porcine tissues, it is readily understood by those of ordinary skill in the art that the technology employed can also be employed with routine variations to other tissues including tissues from avians and other mammals including humans, and the inventors have experimentally confirmed that the methods of the invention can be beneficially employed with frozen and/or lyophilized explant tissues as well as fresh with comparable results.

Tendon and ligament tissues are readily lyophilized using conventional techniques, well known to those of ordinary skill in the art. Lyophilized tissues offer several advantages and are therefore preferred in many potential applications of the technology of the invention. Lyophilized tissues present a smaller load on the vacuum system of the ion beam irradiation tool in preparation for and during the ion irradiation phase of the process, since such lyophilized tissues outgas less vapor than either fresh or frozen tissues. Additionally, lyophilized tissues can be stored without degradation for significant periods of time following irradiation and can be readily shipped or transported by low cost conventional shipping methods to remote sites for their surgical implantation. The lyophilized, irradiated tissues may later be reconstituted (with, for example, physiological saline or with body fluids of the recipient or other suitable fluids) at the location of the surgical procedure shortly prior to surgical implantation. Likewise, the lyophilized, irradiated tissues can be seeded with cells at the location of the surgical procedure shortly prior to surgical implantation. The reconstitution and cell seeding may even be done with cell-containing bodily fluids from the recipient's body to increase compatibility of the graft. Alternatively, the Lyophilized, irradiated tissues can be surgically grafted into the recipient in the lyophilized state, whereupon they come into contact with the recipient's bodily fluids and cells, resulting in in situ reconstitution and cell seeding of the graft tissue at the graft site. In general the long shelf life of the lyophilized, irradiated tissue offers considerable flexibility and practicality to the overall process of preparation and successful implant of graft tissues.

Graft materials explanted for use with the methods of the invention may be taken from a variety of avian and mammalian species (including human) and surgical implantation of graft materials prepared by the methods of this invention can be made into a wide variety of mammal species (including human) and, such grafts may be allografts, autografts, or xenografts, according to the respective donors and recipients of the graft tissues. The techniques for harvesting, growing and seeding new cells onto and into the tissues (including decellularized tissues and/or lyophilized tissues) may employ cells from the prospective graft recipient or from other suitable donor sources according to techniques known to those of ordinary skill in the art. The techniques of explant and decellularization employed in preparing the exemplary porcine ligaments can also be applied to tendon tissue. Accordingly, methods of the invention can be used to remove tendon, ligament or other tissues from a donor (including self-donor) or cadaver to decellularize (when desired) and lyophilize (when desired) and to seed the tissues or decellularized tissues with specific new cells for cellular attachment and proliferation according to techniques known to those of ordinary skill in the art. By use of the irradiation technology, the success of the attachment and proliferation of new cells into the graft material is significantly improved, contributing to an increased likelihood of successful integration of the graft into the recipient and increased likelihood of successful overall medical outcome.

As used herein, the term "biological material" is intended to encompass all tissue materials of biological origin including, without limitation, materials comprising tendon, ligament, bone, cartilage, soft tissues, and other tissues, decellularized or in natural cellularized state, living or dead, fresh, frozen, frozen and thawed, lyophilized, lyophilized and reconstituted, ion irradiated or not. Although the invention has been described with respect to the application of GCIBs formed with particular acceleration potentials and administered at particular doses, it will be realized by those skilled in the art that other doses and acceleration potentials may be employed and that such variations may produces variations in the degree of effects of the GCIB irradiation. Although the invention has been described with respect to the application of GCIBs having gas cluster ions consisting of argon gas, it will be realized by those skilled in the art that other constituent gases and gas mixtures may also be beneficially employed. These include the noble gases, Ne, Ar, Xe, and other gases, including without limitation, the gases oxygen, nitrogen, carbon dioxide, other carbon-containing gases, both organic and inorganic and further including gas mixtures comprising any of these gases mixed with other gases and that such variation may result in variation in the degree and type of effects of the GCIB irradiation. It should be realized that this invention is also capable of a wide variety of further and other embodiments within the spirit and scope of the foregoing disclosure and the appended claims.

What is claimed is:

1. A method for surgical grafting of a tissue, the method comprising:
    explanting a graft tissue from a donor;
    irradiating said graft tissue using a gas-cluster ion beam; and
    surgically grafting said graft tissue into a recipient.

2. The method of claim 1, wherein said donor is a mammalian or an avian species and said recipient is a mammal.

3. The method of claim 2, wherein said graft tissue is an allograft, an autograft or a xenograft.

4. The method of claim 1, wherein said graft tissue is a ligament tissue or a tendon tissue.

5. The method of claim 1, further comprising lyophilizing said graft tissue prior to said irradiating.

6. The method of claim 1, further comprising decellularizing said graft tissue prior to said irradiating.

7. The method of claim 5, further comprising decellularizing said graft tissue prior to said lyophilizing.

8. The method of claim 1, further comprising:
    harvesting cells for seeding; and
    seeding at least a portion of said graft tissue with the harvested cells, prior to said surgical grafting.

9. The method of claim 8, wherein the harvested cells are harvested from said recipient.

10. The method claim 5, further comprising reconstituting said graft tissue after said lyophilizing and said irradiating, and prior to said surgical grafting.

11. The method of claim 8, further comprising reconstituting said graft tissue after said lyophilizing and said irradiating, and prior to said seeding.

12. The method of claim 6, wherein said surgical grafting is bringing said graft tissue into contact with a fluid or cells from said recipient for in situ reconstitution or seeding.

13. The method of claim 5, further comprising transporting said graft tissue to a remote site for said surgical grafting prior to said surgical grafting, 14. A method for surgical grafting, the method comprising:
    explanting a graft tissue from a donor;
    decellularizing said graft tissue;
    lyophilizing said graft tissue;
    irradiating said graft tissue using a gas-cluster ion beam;
    optionally storing said graft tissue for future use;
    optionally transporting said graft tissue to a remote site for surgical grafting;
    optionally seeding cells onto a surface of said graft tissue;
    optionally allowing a desired degree of attachment and proliferation of said cells onto or into said graft tissue; and
    surgically grafting said graft tissue into a recipient.

15. The method of claim 14, wherein said steps of decellularizing and irradiation are done on the same portions of the graft tissue.

16. The method of claim 14, further comprising exposing said graft tissue to a composition comprising a component selected from the group consisting of:
    a growth factor;
    a cytokine:
    a differentiation factor;
    a demineralized bone powder; and
    stem cells.

17. The method of claim 14, wherein said steps of decellularizing and irradiation are done on different portions of the graft tissue.

18. The method of claim 6, wherein said steps of decellularizing and irradiation are done on the same portions of the graft tissue.

19. The method of claim 6, wherein said steps of decellularizing and irradiation are done on different portions of the graft tissue.

* * * * *